United States Patent [19]

Hanover et al.

[11] Patent Number: 5,627,873
[45] Date of Patent: May 6, 1997

[54] MINI C-ARM ASSEMBLY FOR MOBILE X-RAY IMAGING SYSTEM

[75] Inventors: Barry K. Hanover; David E. Barker, both of Salt Lake City; Ross A. Riches, Sandy; Blain C. Erickson, Summit Park; Lonnie B. Weston, Clearfield, all of Utah

[73] Assignee: OEC Medical Systems, Inc., Salt Lake City, Utah

[21] Appl. No.: 511,873

[22] Filed: Aug. 4, 1995

[51] Int. Cl.$^6$ ........................................ H05G 1/02
[52] U.S. Cl. .................... 378/197; 378/196; 378/198
[58] Field of Search .................... 378/193–198, 378/189

[56] References Cited

U.S. PATENT DOCUMENTS

| 4,142,101 | 2/1979 | Yin. |
| 4,481,656 | 11/1984 | Janssen et al. ............... 378/196 |
| B1 4,142,101 | 2/1991 | Yin. |

OTHER PUBLICATIONS

Fluoroscan (brochure), published by FluoroScan Imaging Systems, Inc., Northbrook, Il 60062. no date.
XI SCAN 1000, 12"x12" Track Mounted C–Arm Fluoro System Operating Guide, Part 1: General. no date.

*Primary Examiner*—Don Wong
*Attorney, Agent, or Firm*—Thorpe North & Western, L.L.P.

[57] ABSTRACT

A C-arm apparatus. An X-ray imaging system is coupled to a C-arm, including an X-ray source and an image receptor mounted upon opposing locations, respectively on the C-arm. The C-arm is mass balanced about its axis of orbital rotation and is pivotally coupled to an articulating arm assembly supported upon a wheeled support base. The mass balance enables repositioning of the X-ray imaging system between an anterior-posterior view and an orthogonal lateral view with a single, orbital movement of the C-arm which also causes the views to define an imaging isocenter. The C-arm is preferably miniaturized to an approximate diameter of twenty-eight inches with a source-to-image distance of approximately fourteen inches.

34 Claims, 4 Drawing Sheets

MINI C-ARM ASSEMBLY FOR MOBILE X-RAY IMAGING SYSTEM

BACKGROUND OF THE INVENTION

1. The Field of the Invention

The present invention relates generally to C-arm assemblies in X-ray imaging systems, and more particularly to a miniaturized mobile C-arm assembly which is coupled to an articulating arm assembly and mass balanced about two axes of rotation.

2. The Background Art

It is often desirable to take X-rays of a patient from a number of different positions, preferably without the need for frequent repositioning of the patient. In the particular area of extremities imaging, it is desirable to economize the X-ray system in terms of size and cost without sacrificing the capacity for movability of the X-ray imaging parts to obtain multiple views while the extremity being viewed remains stationary.

Miniaturized X-ray diagnostic equipment has been developed in attempts to meet these needs. However, such prior art equipment, while somewhat useful, is characterized by a number of disadvantages. Multiple portions of the equipment must be adjusted one at a time in order to rotate the imaging X-ray beams without moving the patient. The geometric configuration of the miniature X-ray source holders requires multiple mechanical joints to be locked and unlocked with scrupulous care and attention to sequence in order to reposition the imaging view without causing inadvertent and potentially damaging contact to the extremity being viewed. Further, such prior art equipment is difficult to maneuver in a manner sufficient to achieve an imaging isocenter.

OBJECTS AND SUMMARY OF THE INVENTION

It is therefore an object of the present invention to provide a C-arm apparatus having a rotational X-ray imaging system.

It is another object of the invention, in accordance with one aspect thereof, to provide such an apparatus wherein the X-ray imaging system can be rotatably repositioned with a single joint adjustment.

It is a further object of the invention, in accordance with one aspect thereof, to provide such an apparatus which is capable of providing an imaging isocenter with a single joint adjustment.

It is an additional object of the invention, in accordance with one aspect thereof, to provide such an apparatus which is pivotally manipulable into a compact arrangement for storage.

The above objects and others not specifically recited are realized in a specific illustrative embodiment of a C-arm apparatus. An X-ray imaging system is coupled to a C-arm, including an X-ray source and an image receptor mounted upon opposing locations, respectively on the C-arm. The C-arm is mass balanced about an axis of orbital rotation and is pivotally coupled to an articulating arm assembly supported upon a wheeled support base. The mass balance enables repositioning of the X-ray imaging system between an anterior-posterior view and an orthogonal lateral view with a single, orbital movement of the C-arm which also causes the views to define an imaging isocenter. The C-arm is preferably miniaturized to an approximate outside diameter of twenty-eight inches with a source-to-image distance of approximately fourteen inches.

Additional objects and advantages of the invention will be set forth in the description which follows, and in part will be apparent from the description, or may be learned by the practice of the invention. The objects and advantages of the invention may be realized and obtained by means of the instruments and combinations particularly pointed out in the appended claims.

BRIEF DESCRIPTION OF THE DRAWINGS

The above and other objects, features and advantages of the invention will become apparent from a consideration of the subsequent detailed description presented in connection with the accompanying drawings in which.

DETAILED DESCRIPTION OF PRESENTLY PREFERRED EMBODIMENTS

Figure 1:
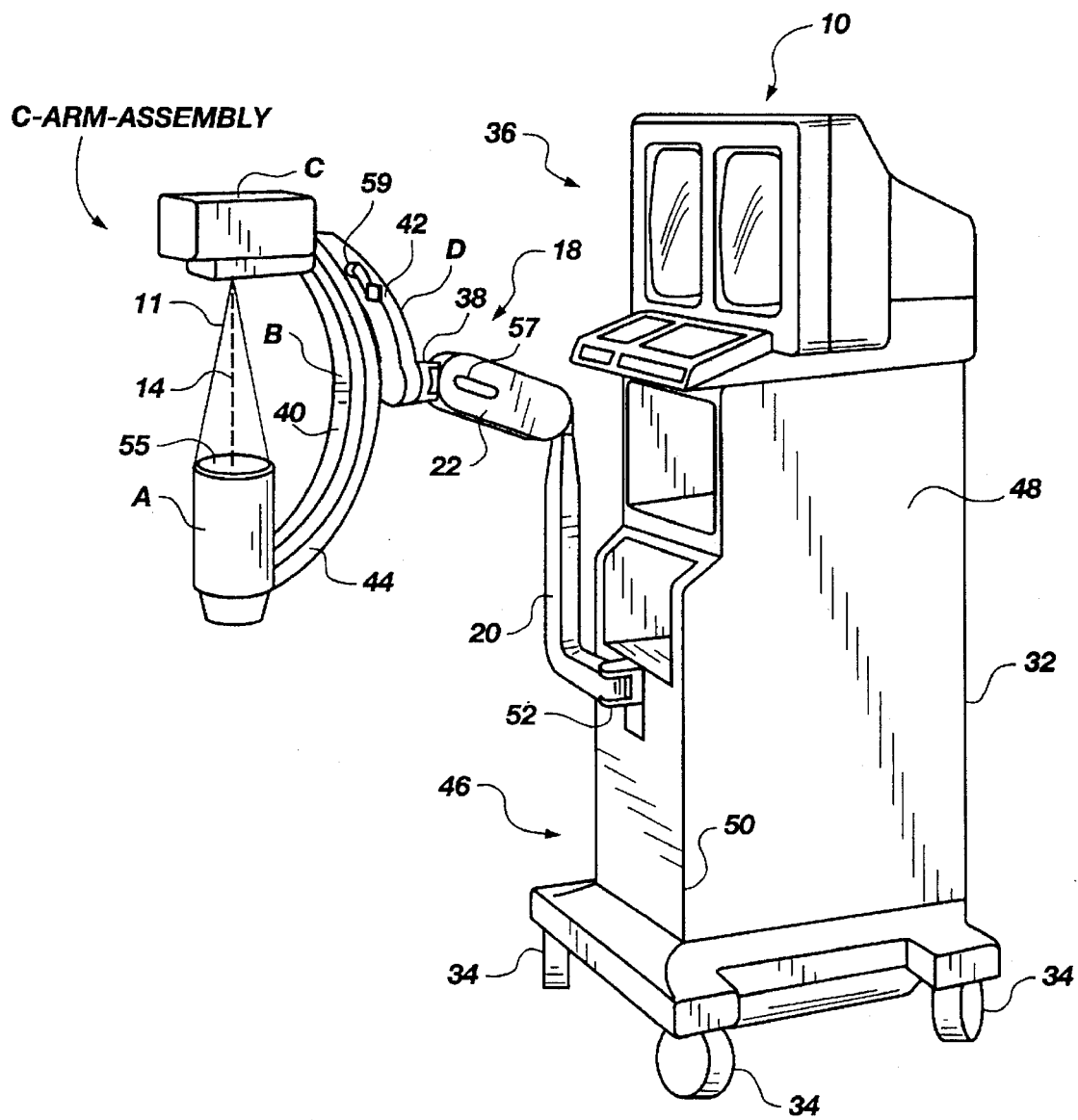
FIG. 1 is a perspective view of a mobile C-arm apparatus and X-ray imaging system made in accordance with the principles of the present invention.

For the purposes of promoting an understanding of the principles in accordance with the invention, reference will now be made to the embodiments illustrated in the drawings and specific language will be used to describe the same. It will nevertheless be understood that no limitation of the scope of the invention is thereby intended. Any alterations and further modifications of the illustrated device, and any additional applications of the principles of the invention as illustrated herein, which would normally occur to one skilled in the relevant art and possessed of this disclosure, are to be considered within the scope of the invention claimed.

Referring now to FIGS. 1–5, there is shown a mobile C-arm apparatus, generally designated at 10. As explained in more detail below, the apparatus 10 is directed to a miniaturized C-arm assembly slidably mounted upon an L-arm or support arm D which is pivotally coupled to an articulating arm assembly supported upon a wheeled base, wherein the C-arm assembly is mass balanced about a single axis of orbital rotation. This mass balancing of the C-arm assembly about the single axis of orbital rotation enables an operator to achieve an imaging isocenter with a single sliding orbital movement of the C-arm assembly. A system which is "mass balanced" as that phrase is used herein refers to a system which is pivotable, orbitable, or otherwise rotatable about an axis which coincides with the center of mass of the system.

The apparatus 10 includes a C-arm assembly, designated generally as C-ARM-ASSEMBLY. The C-ARM-ASSEMBLY has a center of mass $MC_{C\text{-}ARM\text{-}ASSEMBLY}$ and includes a C-arm B having a substantially circular movement track 12 (FIG. 3) formed thereon. An X-ray source C and an image receptor A are mounted upon opposing locations, respectively, on the C-arm B such that the X-ray source and image receptor face each other as shown. The X-ray source C includes means therein for projecting X-rays 11 having a central beam 14 onto the image receptor A. The image receptor A can be an image intensifier or the like, as understood by those of ordinary skill in the art. The X-ray source C and the image receptor A define the source-to-image distance 14 therebetween. The C-ARM-ASSEMBLY is configured and dimensioned such that the source-to-image distance 14 is less than thirty inches. The source-to-image distance can also be less than twenty inches, and preferably less than fifteen inches. Applicants' preferred embodiment is directed to a C-arm B wherein the circular movement track 12 has an outside diameter of approximately fourteen inches with the source-to-image distance 14 also being approximately fourteen inches.

The meaning of the term "central beam" as used herein refers not only to a single center X-ray beam which defines a line extending from the X-ray tube focal spot 15 perpendicularly onto the center of the image receptor screen 55 as known to those skilled in the art, but shall also refer broadly to a cluster of X-ray beams central to the X-ray beams 12 and centered around the single center X-ray beam. Reference numeral 14 shall also refer to the distance between the focal spot 15 of X-ray source A and the image receptor C, known in the art as the source-to-image distance or SID. Applicants' image receptor screen 55 is circular, preferably with a diameter of either four inches or six inches.

Figure 3:
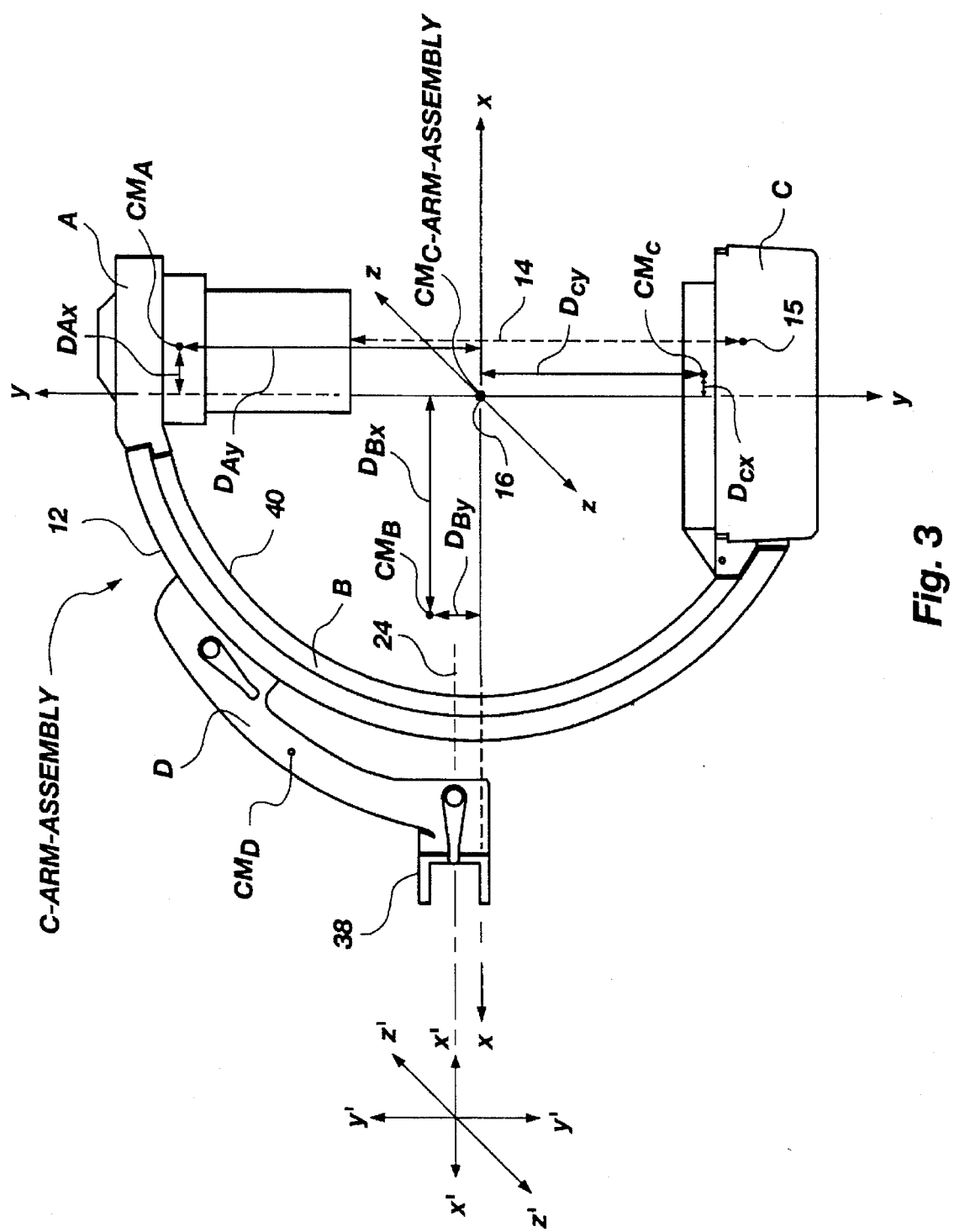
FIG. 3 is a side view of an alternative embodiment of a C-arm assembly portion of the apparatus of FIG. 1.

A support arm D is disposed in slidable engagement with the circular movement track 12 such that the C-ARM-ASSEMBLY is selectively slidable relative to the support arm in orbital rotation about a single axis of orbital rotation 16. FIGS. 1 and 3 illustrate that the orientation of support arm D relative to the X-ray source C and image receptor A may vary, the respective positions of those elements being interposed in FIGS. 1 and 3. The circular movement track 12 is substantially common to a circle having a center point which coincides with the single axis of orbital rotation 16 such that said axis 16 remains substantially fixed relative to the said arm D for any position of the C-ARM-ASSEMBLY relative to said support arm. The term "circular" as used herein shall not be limited in meaning to an actual circle but shall also refer broadly to a partial circle, as in the case of the movement track 12.

Figure 2:
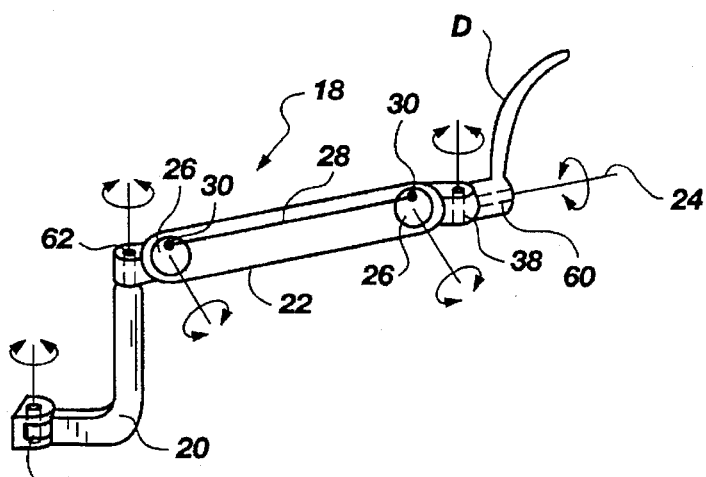
FIG. 2 is a perspective, schematic view of an articulating arm assembly of the apparatus of FIG. 1.

An articulating arm assembly, designated generally at 18, comprises a first arm 20 and a second arm 22 pivotally attached to both the first arm and the support arm D such that the support arm is selectively rotatable relative to the second arm 22 about an axis of lateral rotation 24 (FIG. 3) to selected lateral positions. The second arm 22 of the articulating arm assembly 18 comprises parallel linkage means as known in the art for moving the support arm D and C-ARM-ASSEMBLY relative to the first arm 20 from a first position to a second position such that the rotational axis 24 in the second position is substantially parallel in direction to the rotational axis 24 in the first position. The parallel linkage means is represented in FIG. 2 by a pair of rotational wheels 26 and a rod 28 pivotally coupled at its opposing ends 30 to each wheel 26, respectively, but may also comprise a four-bar parallel linkage as known in the art or the equivalent.

A mobile base support means 32 is pivotally attached to the first arm 20 of the articulating arm assembly 18 for supporting the C-ARM-ASSEMBLY in a suspended position. The mobile base support means preferably comprises a base and wheels 34 rotatably mounted beneath the base to enable the base to roll on the wheels along a floor (not shown). The mobile base support means preferably includes an image processing and display work station as understood by those of ordinary skill in the art, designated generally at 36.

The C-ARM-ASSEMBLY is mass balanced about the single axis of orbital rotation 16 such that the center of mass of the C-arm assembly $CM_{C\text{-}ARM\text{-}ASSEMBLY}$ substantially coincides with the single axis of orbital rotation 16 for any position of said C-ARM-ASSEMBLY relative to the support arm D along the circular movement track 12. Put another way and in reference to the three-dimensional coordinate system x, y and z having an origin at the single axis of orbital rotation 16 represented in FIG. 1:

$$(M_B)(D_{Bx})=(M_A)(D_{Ax})+(M_C)(D_{Cx}), \text{ and} \qquad (1)$$

$$(M_B)(D_{By})+(M_A)(D_{Ay})=(M_C)(D_{Cy}), \qquad (2)$$

where:

$M_B$=mass of C-arm B;

$D_{Bx}$=distance between $CM_B$ and the y-axis;

$CM_B$=center of mass of the C-arm B;

$M_A$=mass of image receptor A;

$D_{Ax}$=distance between $CM_A$ and the y-axis;

$CM_A$=center of mass of the image receptor A;

$M_C$=mass of X-ray source C;

$D_{Cx}$=distance between $CM_C$ and the y-axis;

$CM_C$=center of mass of the X-ray source C and the y-axis;

$D_{By}$=distance between $CM_B$ and the x-axis;

$D_{Ay}$=distance between $CM_A$ and the x-axis; and $D_{Cy}$=distance between $CM_C$ and the x-axis.

Figure 4:
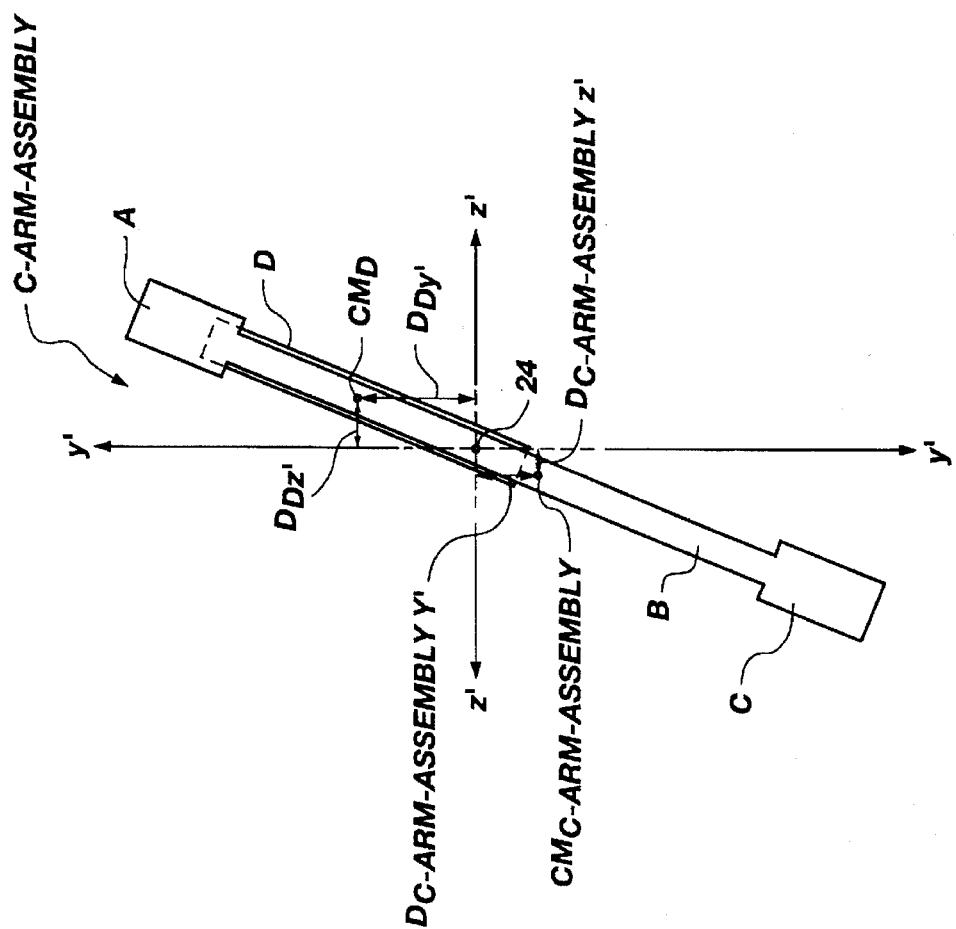
FIG. 4 is a frontal view of the C-arm assembly of FIG. 3.

As shown most clearly in FIG. 4, the C-ARM-ASSEMBLY and the support arm D have a collective center of mass and are collectively mass balanced about the axis of lateral rotation 24 such that said collective center of mass substantially coincides with said axis of lateral rotation 24 for any rotational position of the support arm D relative to the second arm 22 of the articulating arm assembly 18 about said axis of lateral rotation 24. In reference to the three-dimensional coordinate system x', y' and z' having an origin at the axis of lateral rotation 24 represented in FIG. 1 and partially in FIG. 4:

$$(M_{C\text{-}ARM\text{-}ASSEMBLY})(D_{C\text{-}ARM\text{-}ASSEMBLY z})=(M_D)(D_{Dz}), \qquad (3)$$

where:

$M_{C\text{-}ARM\text{-}ASSEMBLY}$=mass of the C-ARM-ASSEMBLY;

$D_{C\text{-}ARM\text{-}ASSEMBLY z}$=distance between $CM_{C\text{-}ARM\text{-}ASSEMBLY}$ and the y'-axis;

$CM_{C\text{-}ARM\text{-}ASSEMBLY}$=center of mass of the C-ARM-ASSEMBLY;

$M_D$=mass of support arm D;

$D_{Dz}$=distance between $CM_D$ and the y'-axis; and $CM_D$=center of mass of the support arm D.

Of course, the equations (1), (2) and (3) apply to the specific configurations and positions illustrated in FIGS. 3–4. Other similar equations consistent with the principles of physics would apply to alternative configurations and positions.

As can be understood by those having ordinary skill in the art, the C-ARM-ASSEMBLY is configured and arranged, in combination with the circular movement track 12 having a sufficient length, to enable the C-ARM-ASSEMBLY to be moveable along the circular movement track 12 in orbital rotation between a first orbital position and a second orbital position such that the central beam 14 in the second orbital position extends in a direction orthogonal to the central beam 14 in the first orbital position. The central beam 14 in the second orbital position passes through a first point of intersection of the central beam in the first orbital position 14, known in the art as an imaging isocenter. This first point of intersection is a first imaging isocenter. The phrase "imaging isocenter" refers to a fixed location of which two different X-ray images of the same area of anatomy may be taken along respective lines of sight. As understood by those skilled in the art of radiology, the imaging isocenter refers to the concept that, in both anterior-posterior and lateral views, the object of imaging interest is centered in the X-ray image of both views without being moved. The apparatus 10 can produce an imaging isocenter automatically without any adjustments other than a single movement of the C-ARM-ASSEMBLY between an anterior-posterior and lateral view.

Preferably, the C-ARM-ASSEMBLY is configured and arranged such that the first point of intersection of the central beam 14 resides closer to the image receptor A than to the X-ray source A. In one particular preferred arrangement, the C-ARM-ASSEMBLY is configured and arranged such that the central beam 14 extends substantially vertically in the first orbital position and substantially horizontally in the second orbital position. The apparatus 10 may be designed with the C-ARM-ASSEMBLY being configured and arranged such that the central beam 14 in the second orbital position substantially coincides with the axis of lateral rotation 24.

The support arm D is pivotally attached and configured at 60 (FIG. 2) relative to the second arm 22 of the articulating arm assembly to enable the C-ARM-ASSEMBLY to rotate about the axis of lateral rotation 24 between a first lateral position and a second lateral position such that the central beam 14 in the second lateral position extends in a direction orthogonal to the central beam 14 in the first lateral position. The central beam 14 in the second lateral position passes through a second point of intersection of the central beam 14 in the first lateral position, the second point of intersection being a second isocenter. If the central beam 14 could be made to coincide with the single axis of orbital rotation 16, and with the axis of lateral rotation 24 when horizontal, and assuming satisfaction of the equations (1), (2) and (3) above, then the first and second imaging isocenters would always coincide and be one and the same point for any combination of lateral and orbitals position of the C-ARM-ASSEMBLY. Even if the central beam 14 does not coincide with the single axis of orbital rotation as in FIG. 3, the first and second imaging isocenters would coincide a majority of the time for any position of the C-ARM-ASSEMBLY if the apparatus 10 can be designed as suggested above wherein the horizontal position of the central beam 14 substantially coincides with the axis of lateral rotation 24.

As a practical matter, the imaging apparatus must be as light as is possible such that it is presently quite difficult to build the apparatus 10 to achieve both (i) a mass balance of the C-ARM-ASSEMBLY about the single axis of orbital rotation 16, and (ii) the central beam 14 coinciding with the single axis of orbital rotation 16. However, applicants have discovered that the miniaturized C-ARM-ASSEMBLY of FIGS. 1–5, wherein the source-to-image distance 14 is less than thirty inches, can be built so that the central beam 14 is sufficiently close to the single axis of orbital rotation 16 that imaging isocentricity is achieved in some form for substantially all combinations of lateral and orbital positions of the C-ARM-ASSEMBLY.

Preferably, the C-ARM-ASSEMBLY is configured and arranged such that the second point of intersection of the central beam resides closer to the image receptor A than to the X-ray source C. Also, preferably, the C-ARM-APPARATUS is configured and arranged such that the central beam 14 extends substantially vertically in the first lateral position and substantially horizontally in the second lateral position.

In accordance with the miniaturized nature of the C-ARM-ASSEMBLY, it is preferred that the circular movement track 12 have a radius which is less than twenty inches, and most preferably less than fifteen inches. The C-arm B includes a circular inner circumference 40 having a radius of less than nineteen inches, and most preferably less than fourteen inches.

Figure 5:
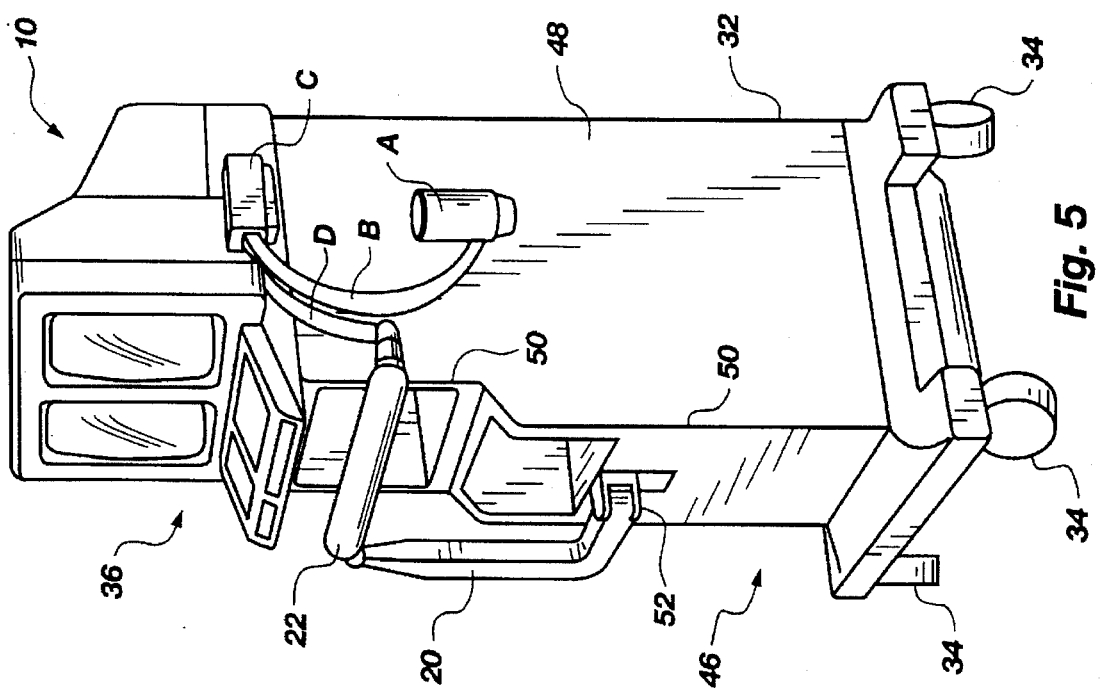
FIG. 5 is a perspective view of the apparatus of FIG. 1 in a folded, compact arrangement for storage.

Referring now more particularly to FIGS. 1 and 5, the apparatus 10 is pivotally manipulable into a compact arrangement for storage as shown. The support arm D and the C-arm B each include a first side panel 42 and 44 (FIG. 1), respectively. The mobile base support means 32 includes a front section 46 and a side section 48 which collectively form a corner section 50 therebetween. The corner section 50 is not necessarily a straight line but may zig-zag or otherwise deviate from a straight line as shown in FIGS. 1 and 5, but is still a corner section. The first arm 20 of the articulating arm assembly 18 is pivotally attached to the front section 46 of the base support means 32 at a first pivot point of attachment 52, and the C-ARM-ASSEMBLY and the articulating arm assembly 18 and the support arm D are configured and pivotally interconnected so as to be pivotally manipulable into a compact arrangement such that (i) the first arm 20 extends from the first pivot point of attachment 52 across at least a portion of the front section 46 of the base support means 32 so as to reside closely adjacent to said front section, and (ii) the second arm 22 extends from the first arm 20 across at least a portion of the front section 46 of the base support means 32 to the corner section 50 so as to reside closely adjacent to said front section 46, and (iii) the support arm D extends from a portion of the second arm 22 adjacent the corner section 50 across at least a portion of the side section 48 of the base support means 32 such that the first side panels 42 and 44 of the support arm D and C-arm B, respectively, reside closely adjacent to said side section 48, such that the second arm 22 and the support arm D collectively extend across at least a portion of the front section 46, around the corner section 50, and across at least a portion of the side section 48.

It is to be understood herein the novel combination embodied in FIG. 5 may also accomplished with equivalent structures. For example, any curved arm member having opposing distal ends may be used in lieu of the circular C-arm B of FIG. 5 as part of a curved arm assembly. It is also to be understood that the C-ARM-ASSEMBLY and its contained X-ray imaging system can be rotatably repositioned, either orbitally about axis 16 or laterally about axis 24, with only a single joint adjustment. The term "joint" refers to any of the slidable and pivotal connections among the C-ARM-ASSEMBLY, support arm D, and articulating arm assembly 18. FIG. 2 shows most of the joints in schematic fashion, including pivotal joints 38, 52, 60, 62, and the wheels 26 and rod 28 schematic of the parallel linkage means. The slidable engagement between the support arm D and the C-arm B is also considered a joint.

Figure 6:
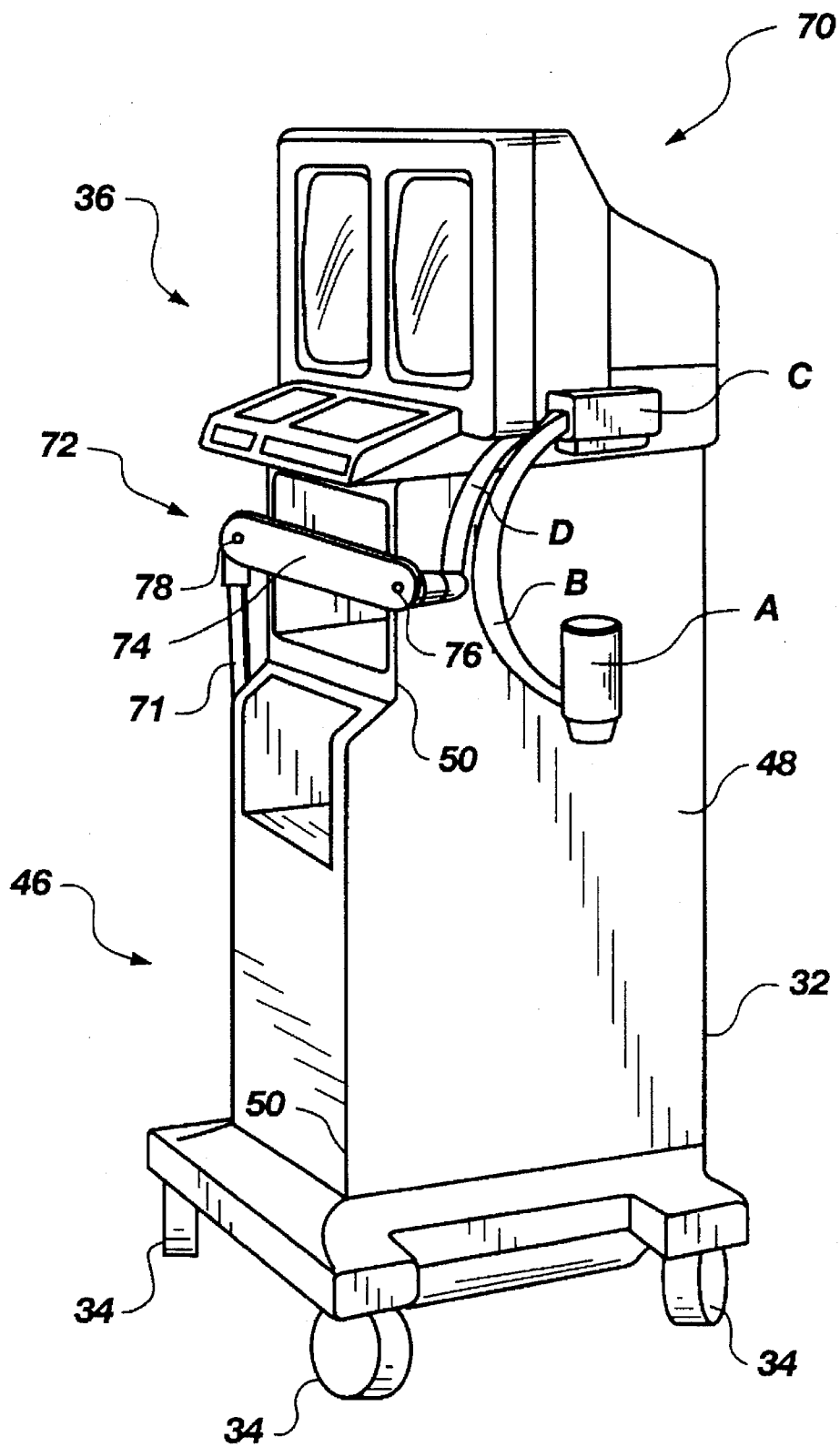
FIG. 6 is a perspective view of an alternative embodiment of the apparatus of FIG. 5.

Referring now to FIG. 6, there is shown at alternative embodiment of the apparatus 10, designated generally at 70. The apparatus 70 includes many of the same structures of the apparatus 10 of FIGS. 1 and 5, such as the X-ray source C and image receptor A, the C-arm B and support arm D, front section 46, side section 48, corner section 50, and the image processing and display work station 36. However, the base support means 32 includes a rigidly attached and upwardly-extending stationary arm 71. The apparatus 70 further includes an alternative articulating arm assembly designated generally at 72, including a first arm 74 pivotally attached to the support arm D at rotational connection 76. The first arm is also pivotally attached to the stationary arm 71 at rotational connection 78. The first arm 74 extends from the base support means 32 (and preferably from the stationary arm 71) across at least a portion of the front section 46. The apparatus 70 is pivotally manipulable in a manner similar to that described above in connection with the apparatus 10 of FIG. 5, in that the first arm 74 and the support arm D collectively extend across at least a portion of the front section 46, around the corner section 50, and across at least a portion of the side section 48.

Many of the advantages of the present invention accrue due to the C-ARM-ASSEMBLY being mass balanced about the single axis of orbital rotation 16, and the combination of the support arm D and the C-ARM-ASSEMBLY being mass balanced about the axis of lateral rotation 24. This configuration enables an operator of the apparatus 10 to produce an imaging isocenter using two orthogonal views which requires the manipulation of only one movement, and thus fewer steps than are required by the prior art miniaturized X-ray imaging systems. In addition, mass balancing about axes 16 and 24 allows those joints to move freely when moved by the operator and yet remain in place when no outside force is being applied to the assembly. As understood to those skilled in the relevant art, locking means 57 and 59 can be used to lock and release movement of some or all of the joints and the like represented schematically in FIG. 2. The compactability of the apparatus 10 illustrated in FIG. 5, combined with the mobility provided by the wheeled base 32 and the manipulability provided by the articulating arm assembly 18 provide the invention with numerous advantages in the field of miniaturized X-ray imaging systems.

It is to be understood that the above-described arrangements are only illustrative of the application of the principles of the present invention. Numerous modifications and alternative arrangements may be devised by those skilled in the art without departing from the spirit and scope of the present invention and the appended claims are intended to cover such modifications and arrangements.

What is claimed is:

1. A mobile C-arm apparatus for use with X-ray diagnostic equipment, said apparatus comprising:

a C-arm assembly having a center of mass, said C-arm assembly further comprising a C-arm having a substantially circular movement track formed thereon, and an X-ray source and an image receptor mounted upon opposing locations, respectively, on the C-arm such that said X-ray source and image receptor face each other, wherein the X-ray source includes means for projecting X-rays having a central beam onto the image receptor;

a support arm disposed in slidable engagement with the circular movement track of the C-arm such that the C-arm assembly is selectively slidable relative to said support arm in orbital rotation about a single axis of orbital rotation, said circular movement track being substantially common to a circle having a center point which coincides with said single axis of orbital rotation such that said single axis of orbital rotation remains substantially fixed relative to the support arm for any position of the C-arm assembly relative to said support arm;

an articulating arm assembly comprising a first arm pivotally attached to the support arm such that the support arm is selectively rotatable relative to said first arm about an axis of lateral rotation to selected lateral positions; and mobile base support means pivotally attached to the first arm for supporting the C-arm assembly in a suspended position, said mobile base support means being moveable along a floor;

wherein the C-arm assembly is mass balanced about the single axis of orbital rotation such that the center of mass of the C-arm assembly substantially coincides with the single axis of orbital rotation for any position of said C-arm assembly relative to the support arm along the circular movement track;

wherein the C-arm assembly and the support arm have a collective center of mass and are collectively mass balanced about the axis of lateral rotation such that said collective center of mass substantially coincides with said axis of lateral rotation for any rotational position of the support arm relative to the first arm of the articulating arm assembly about said axis of lateral rotation.

2. A mobile C-arm apparatus for use with X-ray diagnostic equipment, said apparatus comprising:

a C-arm assembly having a center of mass, said C-arm assembly further comprising a C-arm having a substantially circular movement track formed thereon, and an X-ray source and an image receptor mounted upon opposing locations, respectively, on the C-arm such that said X-ray source and image receptor face each other, wherein the X-ray source includes means for projecting X-rays having a central beam onto the image receptor;

a support arm disposed in slidable engagement with the circular movement track of the C-arm such that the C-arm assembly is selectively slidable relative to said support arm in orbital rotation about a single axis of orbital rotation, said circular movement track being substantially common to a circle having a center point which coincides with said single axis of orbital rotation such that said single axis of orbital rotation remains substantially fixed relative to the support arm for any position of the C-arm assembly relative to said support arm;

an articulating arm assembly comprising a first arm pivotally attached to the support arm such that the support arm is selectively rotatable relative to said first arm about an axis of lateral rotation to selected lateral positions; and mobile base support means pivotally attached to the first arm for supporting the C-arm assembly in a suspended position, said mobile base support means being moveable along a floor;

wherein the C-arm assembly is mass balanced about the single axis of orbital rotation such that the center of mass of the C-arm assembly substantially coincides with the single axis of orbital rotation for any position of said C-arm assembly relative to the support arm along the circular movement track;

wherein the axis of lateral rotation resides above the axis of orbital rotation when the C-arm assembly is being supported by the mobile base support means in a suspended position.

3. The apparatus as defined in claim 1, wherein the X-ray source and an image receptor define a source-to-image distance therebetween, the C-arm assembly being configured and dimensioned such that said source-to-image distance is less than thirty inches.

4. The apparatus as defined in claim 3, wherein the C-arm assembly is configured and dimensioned such that the source-to-image distance is less than twenty inches.

5. The apparatus as defined in claim 3, wherein the C-arm assembly is configured and dimensioned such that the source-to-image distance is less than fifteen inches.

6. The apparatus as defined in claim 1, wherein the first arm of the articulating arm assembly comprises parallel linkage means for moving the support arm and C-arm assembly relative to the base support means from a first position to a second position such that the axis of lateral rotation in the second position is substantially parallel in direction to the axis of lateral rotation in the first position.

7. The apparatus as defined in claim 1, wherein the C-arm assembly is configured and arranged, in combination with the circular movement track having a sufficient length, to enable the C-arm assembly to be moveable along the circular movement track in orbital rotation between a first orbital position and a second orbital position such that the central beam in the second orbital position extends in a direction orthogonal to the central beam in the first orbital position.

8. The apparatus as defined in claim 7, wherein the central beam in the second orbital position passes through a first point of intersection of the central beam in the first orbital position.

9. The apparatus as defined in claim 8, wherein the C-arm assembly is configured and arranged such that the first point of intersection of the central beam resides closer to the image receptor than to the X-ray source.

10. The apparatus as defined in claim 7, wherein the C-arm assembly is configured and arranged such that the central beam extends substantially vertically in the first orbital position and substantially horizontally in the second orbital position.

11. The apparatus as defined in claim 10, wherein the C-arm assembly is configured and arranged such that the central beam in the second orbital position substantially coincides with the axis of lateral rotation.

12. The apparatus as defined in claim 1, wherein the support arm is pivotally attached and configured relative to the first arm of the articulating arm assembly to enable the C-arm assembly to rotate about the axis of lateral rotation between a first lateral position and a second lateral position such that the central beam in the second lateral position extends in a direction orthogonal to the central beam in the first lateral position.

13. The apparatus as defined in claim 12, wherein the central beam in the second lateral position passes through a second point of intersection of the central beam in the first lateral position.

14. The apparatus as defined in claim 13, wherein the C-arm assembly is configured and arranged such that the second point of intersection of the central beam resides closer to the image receptor than to the X-ray source.

15. The apparatus as defined in claim 12, wherein the C-arm apparatus is configured and arranged such that the central beam extends substantially vertically in the first lateral position and substantially horizontally in the second lateral position.

16. The apparatus as defined in claim 1, wherein the mobile base support means comprises a base and wheels rotatably mounted beneath the base to enable the base to roll on the wheels along a floor.

17. The apparatus as defined in claim 16, wherein the mobile base support means includes an image processing and display work station.

18. The apparatus as defined in claim 1, wherein the circular movement track has a radius which is less than twenty inches.

19. The apparatus as defined in claim 18, wherein the radius of the circular movement track is less than fifteen inches.

20. The apparatus as defined in claim 1, wherein the C-arm includes a circular inner circumference having a radius of less than nineteen inches.

21. The apparatus as defined in claim 20, wherein the radius of the C-arm is less than fourteen inches.

22. A mobile C-arm apparatus for use with X-ray diagnostic equipment, said apparatus comprising:

a C-arm assembly having a center of mass, said C-arm assembly further comprising a C-arm having a substantially circular movement track formed thereon, and an X-ray source and an image receptor mounted upon opposing locations, respectively, on the C-arm such that said X-ray source and image receptor face each other, wherein the X-ray source includes means for projecting X-rays having a central beam onto the image receptor;

a support arm disposed in slidable engagement with the circular movement track of the C-arm such that the C-arm assembly is selectively slidable relative to said support arm in orbital rotation about a single axis of orbital rotation, said circular movement track being substantially common to a circle having a center point which coincides with said single axis of orbital rotation such that said single axis of orbital rotation remains substantially fixed relative to the support arm for any position of the C-arm assembly relative to said support arm;

an articulating arm assembly comprising a first arm pivotally attached to the support arm such that the support arm is selectively rotatable relative to said first arm about an axis of lateral rotation to selected lateral positions; and mobile base support means pivotally attached to the first arm for supporting the C-arm assembly in a suspended position, said mobile base support means being moveable along a floor;

wherein the C-arm assembly is mass balanced about the single axis of orbital rotation such that the center of mass of the C-arm assembly substantially coincides with the single axis of orbital rotation for any position of said C-arm assembly relative to the support arm along the circular movement track;

wherein the support arm and the C-arm each include a first side panel, and wherein the mobile base support means includes a front section and a side section which collectively form a corner section therebetween, and wherein the first arm of the articulating arm assembly is pivotally attached to the base support means at a first pivot point of attachment, and wherein the C-arm assembly and the articulating arm assembly and the support arm are configured and pivotally interconnected so as to be pivotally manipulable into a compact arrangement such that (i) the first arm extends from the first pivot point of attachment across at least a portion of the front section of the base support means to the corner section so as to reside closely adjacent to said front section, and (ii) the support arm extends from a portion of the first arm adjacent the corner section across at least a portion of the side section of the base support means such that the first side panels of the support arm and C-arm reside closely adjacent to said side section, such that the first arm and the support arm collectively extend across at least a portion of the front section, around the corner section, and across at least a portion of the side section.

23. A mobile C-arm apparatus for use with X-ray diagnostic equipment, said apparatus comprising:

a curved arm assembly comprising a curved member having a pair of opposing distal ends and an X-ray source and an image receptor mounted upon opposing locations, respectively, on the curved member such that said X-ray source and image receptor face each other, wherein the X-ray source includes means for projecting X-rays having a central beam onto the image receptor;

a support arm coupled to the curved member;

an articulating arm assembly comprising a first arm pivotally attached to the support arm; and base support means pivotally attached to the first arm for supporting the curved arm assembly in a suspended position;

wherein the support arm and the curved member each include a first side panel, and wherein the base support means includes a front section and a side section which collectively form a corner section therebetween, and wherein the first arm of the articulating arm assembly is pivotally attached to the base support means at a first pivot point of attachment, and wherein the curved arm assembly and the articulating arm assembly and the support arm are configured and pivotally interconnected so as to be pivotally manipulable into a compact arrangement such that (i) the first arm extends from the first pivot point of attachment across at least a portion of the front section of the base support means to the corner section so as to reside closely adjacent to said front section, and (ii) the support arm extends from a portion of the first arm adjacent the corner section across at least a portion of the side section of the base support means such that the first side panels of the support arm and curved member reside closely adjacent to said side section, such that the first arm and the support arm collectively extend across at least a portion of the front section, around the corner section, and across at least a portion of the side section.

24. The apparatus as defined in claim 23, wherein the curved member comprises a C-arm having a substantially circular movement track formed thereon, and wherein the support arm is disposed in slidable engagement with the circular movement track of the C-arm such that the curved arm assembly is selectively slidable relative to said support arm in orbital rotation, and wherein the support arm is selectively rotatable relative to the second arm about an axis of lateral rotation to selected lateral positions, and wherein the base support means comprises a mobile base being moveable along a floor.

25. The apparatus as defined in claim 24, wherein the circular movement track is substantially common to a circle having a center point such that the curved arm assembly is selectively slidable relative to the support arm in orbital rotation about a single axis of orbital rotation, said single axis of orbital rotation being substantially common to the center point, such that said single axis of orbital rotation remains substantially fixed relative to the support arm for any position of the curved arm assembly relative to said support arm.

26. The apparatus as defined in claim 25, wherein the curved arm assembly has a center of mass and wherein said curved arm assembly is mass balanced about the single axis of orbital rotation such that the center of mass of the curved arm assembly substantially coincides with the single axis of orbital rotation for any position of said curved arm assembly relative to the support arm along the circular movement track.

27. The apparatus as defined in claim 23, wherein the base support means includes a rigidly attached and upwardly-extending stationary arm, and wherein the first arm of the articulating arm assembly is pivotally attached to said stationary arm.

28. A mobile C-arm apparatus for use with X-ray diagnostic equipment, said apparatus comprising:

a curved arm assembly comprising a curved member having a pair of opposing distal ends and an X-ray source and an image receptor mounted upon opposing locations, respectively, on the curved member such that said X-ray source and image receptor face each other, wherein the X-ray source includes means for projecting X-rays having a central beam onto the image receptor;

a support arm coupled to the curved member;

an articulating arm assembly comprising a first arm and a second arm pivotally attached to both the first arm and the support arm; and base support means pivotally attached to the first arm of the articulating arm assembly for supporting the curved arm assembly in a suspended position;

wherein the support arm and the curved member each include a first side panel, and wherein the base support means includes a front section and a side section which collectively form a corner section therebetween, and wherein the first arm of the articulating arm assembly is pivotally attached to the front section of the base support means at a first pivot point of attachment, and wherein the curved arm assembly and the articulating arm assembly and the support arm are configured and pivotally interconnected so as to be pivotally manipulable into a compact arrangement such that (i) the first arm extends from the first pivot point of attachment across at least a portion of the front section of the base support means so as to reside closely adjacent to said front section, and (ii) the second arm extends from the first arm across at least a portion of the front section of the base support means to the corner section so as to reside closely adjacent to said front section, and (iii) the support arm extends from a portion of the second arm adjacent the corner section across at least a portion of the side section of the base support means such that the first side panels of the support arm and curved member reside closely adjacent to said side section, such that the second arm and the support arm collectively extend across at least a portion of the front section, around the corner section, and across at least a portion of the side section.

29. A mobile C-arm apparatus for use with X-ray diagnostic equipment, said apparatus comprising:

a C-arm assembly having a center of mass, said C-arm assembly further comprising a C-arm having a substantially circular movement track formed thereon, and an X-ray source and an image receptor mounted upon opposing locations, respectively, on the C-arm such that said X-ray source and image receptor face each other, wherein the X-ray source includes means for projecting X-rays having a central beam onto the image receptor;

a support arm disposed in slidable engagement with the circular movement track of the C-arm such that the C-arm assembly is selectively slidable relative to said support arm in orbital rotation about a single axis of orbital rotation, said circular movement track being substantially common to a circle having a center point which coincides with said single axis of orbital rotation such that said single axis of orbital rotation remains substantially fixed relative to the support arm for any position of the C-arm assembly relative to said support arm;

an articulating arm assembly comprising a first arm pivotally attached to the support arm such that the support arm is selectively, laterally rotatable relative to said first arm about a first axis of rotation to selected lateral positions; and mobile base support means pivotally attached to the first arm for supporting the C-arm assembly in a suspended position, said mobile base support means being moveable along a floor;

wherein the C-arm assembly is mass balanced about the single axis of orbital rotation such that the center of mass of the C-arm assembly substantially coincides with the single axis of orbital rotation for any position of said C-arm assembly relative to the support arm along the circular movement track;

wherein the articulating arm assembly further comprises means for enabling the support arm to rotate relative to the first arm also about a second axis of rotation which is noncoaxial with respect to the first axis of rotation.

30. The apparatus as defined in claim 29, wherein the first and second axes of rotation are substantially orthogonal to each other.

31. The apparatus as defined in claim 30, wherein the articulating arm assembly further comprises means for enabling the first arm to rotate relative to the mobile base support means about a third axis of rotation which is noncoaxial with respect to the first axis of rotation.

32. The apparatus as defined in claim 31, wherein the second and third axes of rotation are substantially parallel to each other and extend in a substantially vertical direction when the C-arm assembly is supported in the suspended position by the mobile base support means.

33. The apparatus as defined in claim 31, wherein the articulating arm assembly comprises a second arm pivotally attached at one end thereof to the first arm, wherein said second arm is also pivotally attached at an opposing end thereof to the mobile base support means such that said first and second arms are rotatable about a fourth axis of rotation which is noncoaxial with respect to the first axis of rotation.

34. The apparatus as defined in claim 33, wherein the second, third and fourth axes of rotation are substantially parallel to each other and extend in a substantially vertical direction when the C-arm assembly is supported in the suspended position by the mobile base support means.

* * * * *

REEXAMINATION CERTIFICATE (4017th)

United States Patent [19]
Hanover et al.

[11] B1 5,627,873
[45] Certificate Issued Mar. 14, 2000

[54] MINI C-ARM ASSEMBLY FOR MOBILE X-RAY IMAGING SYSTEM

[75] Inventors: Barry K. Hanover; David E. Barker, both of Salt Lake City; Ross A. Riches, Sandy; Blain C. Erickson, Summit Park; Lonnie B. Weston, Clearfield, all of Utah

[73] Assignee: OEC Medical Systems, Salt Lake City, Utah

Reexamination Request:
No. 90/005,008, Jun. 5, 1998

Reexamination Certificate for:
Patent No.: 5,627,873
Issued: May 6, 1997
Appl. No.: 08/511,873
Filed: Aug. 4, 1995

[51] Int. Cl.[7] ....................................................... H05G 1/02
[52] U.S. Cl. ............................ 378/197; 378/196; 378/198
[58] Field of Search ............................. 378/189, 193–198

[56] References Cited

U.S. PATENT DOCUMENTS

| | | |
|---|---|---|
| Re. 34,943 | 5/1995 | Van Endschot et al. . |
| 3,281,598 | 10/1966 | Hollstein . |
| 4,209,706 | 6/1980 | Nunan . |
| 4,447,721 | 5/1984 | Wang . |
| 4,716,581 | 12/1987 | Barud . |
| 4,768,216 | 8/1988 | Harvey et al. . |
| 4,797,907 | 1/1989 | Anderton . |
| 4,955,046 | 9/1990 | Siczek et al. . |
| 4,961,214 | 10/1990 | Van Endschot et al. . |
| 5,014,293 | 5/1991 | Boyd et al. . |
| 5,038,371 | 8/1991 | Janssen et al. . |
| 5,050,204 | 9/1991 | Siczek et al. . |
| 5,067,145 | 11/1991 | Siczek et al. . |
| 5,226,069 | 7/1993 | Narita . |
| 5,283,808 | 2/1994 | Cramer et al. . |
| 5,426,683 | 6/1995 | O'Farrell, Jr. et al. . |
| 5,475,730 | 12/1995 | Galando . |
| 5,506,882 | 4/1996 | O'Farrell, Jr. et al. . |
| 5,583,909 | 12/1996 | Hanover . |
| 5,617,462 | 4/1997 | Spratt . |
| 5,627,873 | 5/1997 | Hanover et al. . |
| 5,642,395 | 6/1997 | Anderton et al. . |

FOREIGN PATENT DOCUMENTS

| | | |
|---|---|---|
| 0 023 051 | 1/1981 | European Pat. Off. . |
| 0 488 991 A1 | 5/1987 | European Pat. Off. . |
| 0 430 338 | 6/1991 | European Pat. Off. . |
| WO 95/25419 | 9/1995 | European Pat. Off. . |
| 3138916 A1 | 9/1981 | Germany . |
| 85 21 246 U | 7/1985 | Germany . |
| 89 06 386 U | 5/1989 | Germany . |
| 40 37 054 C1 | 11/1990 | Germany . |
| 2098 440 | 11/1982 | United Kingdom . |

OTHER PUBLICATIONS

International ISS Surgical Systems, Inc., ISS–2000 Plus Multispecialty Surgical Imaging System Brochure, pp. 1–25, 1991, Phoenix, Arizona.

*Primary Examiner*—David P Porta

[57] ABSTRACT

A C-arm apparatus. An X-ray imaging system is coupled to a C-arm, including an X-ray source and an image receptor mounted upon opposing locations, respectively on the C-arm. The C-arm is mass balanced about its axis of orbital rotation and is pivotally coupled to an articulating arm assembly supported upon a wheeled support base. The mass balance enables repositioning of the X-ray imaging system between an anterior-posterior view and an orthogonal lateral view with a single, orbital movement of the C-arm which also causes the views to define an imaging isocenter. The C-arm is preferably miniaturized to an approximate diameter of twenty-eight inches with a source-to-image distance of approximately fourteen inches.

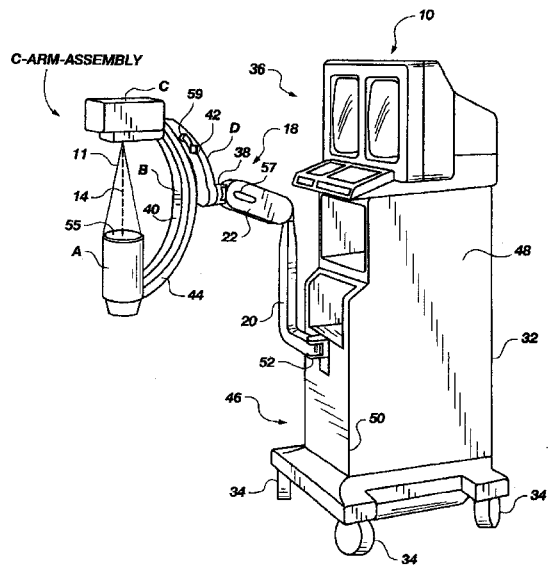

REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1–34 is confirmed.

* * * * *